United States Patent [19]

Cowfer et al.

[11] Patent Number: 5,750,812
[45] Date of Patent: May 12, 1998

[54] METHOD FOR REDUCING FORMATION OF POLYCHLORINATED AROMATIC COMPOUNDS DURING AIR OXYCHLORINATION OF $C_1$-$C_3$ HYDROCARBONS

[75] Inventors: Joseph Allen Cowfer, Avon Lake; Victor James Johnston, Silver Lake, both of Ohio; Lawrence Popiel, Houston, Tex.

[73] Assignee: The Geon Company, Avon Lake, Ohio

[21] Appl. No.: 581,238

[22] Filed: Dec. 28, 1995

[51] Int. Cl.$^6$ .................. C07C 17/154; C07C 17/156
[52] U.S. Cl. .................................. 570/245; 570/243
[58] Field of Search ............................. 570/243, 245

[56] References Cited

PUBLICATIONS

Born, J., et al. Fly Ash Mediated Oxychlorination of Phenol and its Role in PCDD/F Formation, Chemosphere, vol. 26, No. 12, pp. 2087–2095, 1993.
Stromberg, B., Low Temperature Formation and Minimization of Chlorinated Hydrocarbons, Chemosphere, vol. 23, Nos. 8–10, pp. 1515–1525, 1991.
Steiglitz, M., Formation of Organic Compounds from Toluene with Fly Ash as Catalyst, Chemosphere, vol. 27, Nos. 1–3, pp. 179–186, 1993.
Low Temperature Formation and Minimization of Chlorinated Hydrocarbons, Stromberg, Chemosphere, vol. 23, pp. 1515–1525, (1991).
Methane, Hydrogen Chloride and Oxygen Form a Wide Range of Chlorinated Organic Species in the Temperature Range 400°C.–950°C., E. Klund, et al., Chemosphere, vol. 17, No. 3, pp. 575–586 (1988).
Denovo Synthesis of PCDD, PCDF, PCB, PCN, and PAH in a Pilot Incinerator, Benfenati, et al., Chemosphere, vol. 22, No. 11 pp. 1045–1052 (1991).

Effect of Temperature, Carrier Gas and Precursor Structure on PCDD and PCDF formed from precursors by Catalytic Activity of MSW Incinerator Fly Ash, Ross, et al., Chemosphere, vol. 19 Nos. 1–6, pp. 291–298, (1989).

*Formation of PCDFs, PCDDs and Related Compounds by Oxychloringation of Ethane*, Evers, MTC Publication No. MTC89EE, (1989). English Translation from Dutch.

*Primary Examiner*—S. Mark Clardy
*Attorney, Agent, or Firm*—Joe A. Powell

[57] ABSTRACT

An improved process is disclosed for manufacturing chlorinated hydrocarbon by way of a once-through air-based oxychlorination process which yields reduced levels of environmental toxins such as chlorobenzenes, polychlorinated biphenyls, polychlorinated dibenzodioxins and polychlorinated dibenzofurans. The process involves fixed bed or fluid bed catalyzed oxychlorination of a hydrocarbon reactant containing from 1 to 3 carbon atoms. The oxychlorination process consists of contacting the hydrocarbon reactant with air or oxygen enriched air and hydrogen chloride in the presence of the oxychlorination catalyst in a heated reaction zone operated at from 150° C. to 600° C. and recovering chlorinated hydrocarbon from the effluents of the reaction zone. The improvement consists of the use of air which is pretreated before use in the operated oxychlorination process by a means for removal of the aromatic hydrocarbons.

6 Claims, No Drawings

METHOD FOR REDUCING FORMATION OF POLYCHLORINATED AROMATIC COMPOUNDS DURING AIR OXYCHLORINATION OF $C_1$-$C_3$ HYDROCARBONS

FIELD OF THE INVENTION

The present invention relates to processes involving oxychlorination of $C_1$-$C_3$ hydrocarbons especially methane, ethane, propane, ethylene, propylene, acetylene, and propyne using ambient air as the oxygen source.

BACKGROUND OF THE INVENTION

Some commercial uses of chlorine give rise to small but measurable quantities of polychlorinated aromatic compounds such as chlorobenzenes, polychlorinated biphenyls (PCBs), polychlorinated dibenzodioxins (PCDDs) and polychlorinated dibenzofurans (PCDFs) the latter two of which are hereinafter referred to as PCDD/F(s) and are considered environmentally toxic. The polychlorinated aromatics such as PCB, PCDD and PCDF are undesirable compounds, all of which are referred to collectively herein as HUCs, and have been found in soil and lake sediments and their reduction or elimination from industrial production is becoming of increasing concern. The literature references PCDD/F formation as unavoidable for many industrial chlorine processes, especially for the oxychlorination of ethylene to 1,2-dichloroethane, also referred to as ethylene dichloride (EDC), the principal intermediate in the production of vinyl chloride monomer (VCM).

Minute quantities of PCDD/Fs have been monitored in a variety of industries, including solid waste incinerators, EDC/VCM processes and other processes that involve the chlorination, oxychlorination or hydrochlorination of non-aromatic hydrocarbons, including the reverse processes, i.e. dechlorination or dehydrochlorination. A recent report compiled from case studies of emissions from EDC/VCM processes in Europe estimates annual emissions of what are referred to as toxic equivalents of 2,3,7,8-tetrachloro dibenzodioxin (TCDD) at 1.8 kg. See *De Vorming van PCDFs, PCDDs en Gerelateerde Verbindingen Bij de Oxychlorination van Etheen*, Evers, E. H. G., Dept. of Environmental Toxicology, University of Amsterdam, Contract No. ZH4005, Nat. Water Service District of So. Holland (hereinafter referred to as the NWS Study) 1989. MTC Pub. No. MTC89EE. Moreover, experts are in disagreement over what levels of these toxins are generated from both natural and industrial processes.

There are numerous literature citations of investigations concerning the various synthetic routes giving rise to PCDD/Fs. *Chemosphere*, Vol. 23, Nos. 8–10, O. Hutzinger, Editor, Pergamon Press, 1991. By way of summary, the significant precursors that may lead to the formation of PCDD/Fs noted in the literature include chlorophenol, benzene, chlorinated benzene, and diphenyl ether. These species have been found to convert to PCDD/Fs via condensation, free-radical and ionic mechanisms. *Chlorinated Dioxins and Related Compounds*, O. Hutzinger, et. al. Editors, Pergamon Press, 1982.

The de novo synthesis of PCB's and PCDD/Fs from non-aromatic precursors (including elemental forms) has been reported in the literature for oxychlorination processes. *Chemosphere*, Eklund, G.; Pederson, J. R.; Stromberg, B., 17, 575, 1988. The term de novo is defined as formation of PCDD/Fs directly from acyclic, aliphatic hydrocarbon, such as methane and ethylene, in the presence of oxygen and HCl.

For example, the NWS study demonstrated that a number of PCDD/Fs were detected in the gas phase and catalyst residue of a simulated oxychlorination process. The total amount of PCDD/F's observed in the NWS experiments was 546 nanograms per 1.31 grams of EDC formed or 417 ng/g (ppb). The PCDD/Fs congener pattern formed in the NWS experiments was very similar to that found in the waste sludge of the VCM industries along the Rhine river basin and indicates that the laboratory study accurately modeled the process occurring in commercial units. The authors of the NWS Study concluded that copper catalyst plays a role in formation of PCDD/Fs in mediums in which carbon, chlorine, oxygen and active catalytic surfaces are present. The data confirms the conclusion that PCDD/Fs are unavoidable and formed de novo in the oxychlorination of alkanes and alkenes, e.g ethylene. The researchers presumed that aromatization of simple carbon structures was occurring in order to account for the apparent de novo synthesis.

De novo formation of traces of chlorinated alkenes, benzenes, -phenols and biphenyl has also been reported to be formed by the reaction of $CO_2$ and HCl in the presence of catalysts. *Chemosphere*, Stromberg, B. 27, 179, 1993; *Chemosphere*, 23, 1515, 1990. These catalysts include many commercially used materials like those used in oxychlorination processes. In addition, fly ash from municipal solid waste incinerators has also been shown to catalyze formation of PCDD/Fs. a) *Chemosphere*, Ross, B. J.; Naikwadi, K. P.; Karasek, F. W., 19,291, 1989; b) *Chemosphere*, Benfenati, E.; Mariani, G.; Fanelli, R.; Zuccotti, S., 22, 1045, 1992; and *Chemosphere*, Born J. G. P.; Louw, R.; Mulder, P., 26, 2087, 1993. One such study has shown that favorable conditions occur at temperatures between 280° C. and 300° C., leading to a consensus among investigators of incineration methods that PCDD/Fs likely form in the post-combustion vent gas cooling zones of solid waste incinerators. Thus, studies have shown that de novo synthesis of chlorinated aromatic compounds apparently occurs under a variety of conditions.

With the many reports of de novo formation of PCDD/Fs in industrial chlorine consuming processes, reduction or elimination of these by-products is highly sought but apparently an elusive goal. Despite this evidence, some approaches have focused on improving the reaction selectivity to making the desired product hence less amounts of undesirable by products. For example, one approach which is considered from the standpoint of reduction in the level of byproducts produced in the manufacture of EDC, is the improved direct chlorination process disclosed in U.S. Pat. No. 4,410,747 ('747). This liquid phase reaction of ethylene and chlorine as taught in '747 is conducted at the boiling point of the EDC liquid in the presence of a metal chloride catalyst and added aromatic hydrocarbon, such as benzene. The side reactions forming undesired by-products, principally 1,1,2-trichloroethane, are reduced. Following the view that de novo synthesis of PCDD/Fs is occurring, improved reaction selectivity could reduce the level of de novo PCDD/Fs formed.

Other improvements taught in the art have focused on reduction in the volume of waste effluent discharged from the oxychlorination process. In the balanced process for oxychlorination of ethylene to make EDC, there is provided the recapture and re-use of hydrogen chloride from the cracking of 1,2-dichloroethane to vinyl chloride monomer.

The amount of waste effluent is reduced considerably in the re-use of HCl. This recycled HCl is typically separated from EDC, VCM and byproducts by distillation. Hence, reducing the volume of waste would improve environmental impact however, with respect to HUCs, reducing the absolute levels is still of paramount concern.

In recent practice there have been further reductions in the volume of effluent from oxychlorination processes by incorporating a vent recycle system. In this process, the reaction gases from the catalytic process are cooled under pressure in one or more condensation stages. Water and condensed EDC are removed and the bulk of unreacted starting gases and inert gas are re-pressurized and recycled to the oxychlorination reactor. The recycle method, used in conjunction with oxygen feed rather than air, reduces the vent gas volumes to only a small fraction of that produced in the once-through, air-based process. There are many advantages in utilizing the vent recycle process mainly in terms of efficiencies, however with respect to PCDD/Fs, there is no advantage in recycling vent gases, since PCDD/F compounds are condensed as heavy ends. Moreover, the present invention is directed to the once-through method using air as the principal oxygen source.

A laboratory investigation comparing PCDD/F formation for the air based oxychlorination and the oxygen based method was undertaken. This study revealed that PCDD/Fs are formed to a greater extent with the air-based process. This was surprising since in these experiments, the only difference from a practical and theoretical standpoint was the source of oxygen. Based on aforementioned research studies showing the de novo synthesis of PCDD/Fs, one would have expected the same levels of PCDD/F formed regardless of the oxygen source. The difference remained unaccounted for. The practice of air-based oxychlorination is an established industrial process worldwide. In some parts of the world, pure oxygen is unavailable or too costly which leaves the air based process as the only available approach. Therefore, a cost effective reduction in the amount of PCDD/F formed in the air-based oxychlorination process would be a valuable improvement.

In careful quantitative measurements of laboratory oxychlorination processes utilizing copper (II) catalyst, using both air and oxygen, there was found measurable levels of PCDD/F which were accounted for surprisingly not from de novo synthesis, but from trace levels of aromatic compounds contained in the ambient air. The finding that de novo synthesis did not occur in a properly controlled oxychlorination process now provides the benefit that by eliminating trace aromatic compounds present in ambient air, the incidence of PCDD/Fs can be reduced or eliminated entirely. The novel approach therefore is based on eliminating the sources of precursor compounds which may form PCDD/Fs in oxychlorination as preferable to an approach which otherwise assumes their unavoidable formation and focuses on down-stream isolation and waste disposal after incidental formation. The fact revealed herein is that these compounds are not unavoidable.

SUMMARY OF THE INVENTION

In accordance with the invention there is provided an operated oxychlorination process for manufacturing chlorinated hydrocarbon. The process involves fixed bed or fluid bed catalyzed oxychlorination of a hydrocarbon reactant containing from 1 to 3 carbon atoms. The oxychlorination process comprises contacting a $C_1$–$C_3$ hydrocarbon reactant with air and HCl. The feedstocks are reacted in the presence of the oxychlorination catalyst in a heated reaction zone operated at from 150° C. to 600° C. wherein chlorinated hydrocarbon product is recovered from the effluents of the reaction zone. The process is characterized by the fact that air is treated before use in the operated oxychlorination process by a means for removal of aromatic hydrocarbons.

DETAILED DESCRIPTION

The present invention stems from the unexpected discovery that the de novo synthesis of PCDD/Fs is not a necessary result in oxychlorination of non-aromatic hydrocarbons under industrially practiced conditions. It has been shown that a major amount of PCDD/Fs found in the effluent of the air-based oxychlorination process is contributed not by de novo synthesis during the oxychlorination of aliphatic hydrocarbon but from a low level of aromatic compounds discovered in the air feedstream. These aromatic compounds are removed from the air by conventional means, prior to usage in the present invention oxychlorination process, thus preventing their conversion to PCB's and PCDD/Fs during oxychlorination.

Removal of aromatic compounds by air distillation includes the steps of condensing air in a vessel equipped with a condenser, followed by separating condensed vapors from non-condensable gases. The vaporizing and condensing steps preferably include a means for providing a countercurrent, multistage fractionation as is widely used in distilling a variety of liquids.

Other processes for treating air for the removal of trace aromatic compounds are known in the art such as passing air through a vessel containing solid or liquid adsorbent or absorbent. Solid adsorbents known in the art and include, but are not limited to, activated carbon, zeolite, alumina, diatomaceous earth, various forms of silica such as silica gel, and supported, selective adsorbing or absorbing polymer resin. Liquid absorbents include but are not limited to paraffins, eg. aliphatic hydrocarbons such as pentanes, hexanes, $C_5$–$C_9$ distillate fractions, and the like, and water.

Removal of aromatic compounds from air can also be accomplished by conversion to non-aromatic species by hydrogenation reactions which include the treatment of air with hydrogenation metal catalyst such as nickel, platinum or palladium in the presence of a hydrogen source to convert the aromatic compounds to saturated cyclic aliphatic compounds.

Catalytic oxidation over an oxidation catalyst in the presence of oxygen to convert the aromatic compounds to carbon dioxide and water is another suitable means for removal of aromatic compounds from air.

The particular method of removing aromatic compounds from air is not critical so long as the method chosen effectively reduces the level of aromatic compounds in air to less than about 0.1 parts per trillion (or 0.1 ng/g), and may be chosen by the practitioner merely on the basis of available equipment and preferred economics which are beyond the scope of this disclosure. Furthermore, the method chosen can be made on the basis of the level of aromatic compounds present in the ambient air at a particular location. For instance, the Houston Regional Monitoring Network measured an annual mean benzene concentration in air ranging from 1 to 3.5 parts per billion volume basis in 1990. Other areas may contain higher or lower levels. Among the pretreatment steps available, preferred methods include treatment with an oxidation catalyst, passing air through an adsorbing column containing activated carbon, and extraction with paraffin liquids.

In another aspect of the invention, there is provided an improved oxychlorination process effluent, the waste portion of which contains reduced, and preferably less than 0.1 parts per billion of polychlorinated aromatics, the process effluent is produced in an oxychlorination process by contacting with an oxychlorination catalyst in a heated reaction zone operating at from 150° C. to 600° C., a $C_1$ to $C_3$ hydrocarbon reactant, such as methane, ethane, ethylene, propane, propylene, acetylene, propyne, chloroethane, chloropropane, dichloromethane, dichloroethane, and the like, in the presence of air, and hydrogen chloride.

Suitable catalysts used in the oxychlorination process are known and understood conventionally. Examples are disclosed in U.S. Pat. Nos. 3,624,170, 4,446,249, 4,740,642, and 5,011,808 and European Patent Publication No. 0255156. The process conditions required in catalytic oxychlorination are also known and established in the art. Examples are described in U.S. Pat. No. 3,488,398 to Harpring et al. Oxychlorination catalysts are suitable either in the form of fixed bed types or fluid bed types.

In the case of oxychlorination of saturated hydrocarbons containing 1, 2 or 3 carbon atoms the heated reaction zone is operated generally from 300° C. to 600° C. In the case of oxychlorination of unsaturated hydrocarbons containing 2 or 3 carbon atoms, the heated reaction zone is operated from 150° C. to 300° C. Halogenated derivatives can also be advantageously chlorinated using the present process and include chloromethane, dichloromethane, chloroethane, dichloroethane, trichloroethane, fluoromethane, fluoroethane, fluoropropane, chlorofluoromethane, chlorofluoroethane, chlorofluoropropane, and bromo-substituted $C_1$–$C_3$ hydrocarbons. The process is operated at atmospheric pressure or above atmospheric pressure. The molar ratios of reactant feed gases $HCl/C_2H_4/O_2$ are generally maintained at 2/1–1.5/0.5–1.0. Further treatment of the chlorinated product is possible using conventional thermal cracking and/or purification means established in the art.

EXPERIMENTS

Several experiments were performed to demonstrate that the careful removal of aromatic compounds from air streams used as the oxygen source for oxychlorination processes leads to a significant reduction in the amount of PCBs and PCDD/Fs.

Reactions were performed in laboratory scale fluid-bed oxychlorination reactors operated between 210° C. and 245° C., contact time of from 15 and 40 seconds and otherwise, within the operating range of commercial units. Contact time is defined as the fluidized bed volume of the catalyst bed divided by the volumetric flow rate of the sum of all the feed gases at reactor control temperature and reactor top pressure. In some experiments, previously measured levels of aromatic compounds were allowed to enter the reactor with the feed gases. Other experiments involved the artificial addition of benzene, dichlorobenzene, or toluene as model compounds. Baseline control experiments were performed wherein no aromatic compounds were present in the feed or on the catalyst.

It is reported in the scientific literature dealing with quantitative analysis of PCBs and PCDD/Fs that the PCBs and particularly PCDD/Fs formed in oxychlorination and other processes accumulate and become concentrated on the catalyst and are found in residues extractible from the solid catalyst particles. *De Vorming van PCDFs, PCDDs en Gerelateerde Verbindingen Bij de Oxychlorination van Etheen,* Evers, E. H. G., Doctoral Thesis, University of Amsterdam, 1989. MTC Pub. No. MTC89EE. In the experimental work summarized below, analyses were performed on both the reactor effluent (product and gases) and the solid catalyst particles. For analytical consistency and simplicity, only results of analyses on residues from catalyst samples are reported below.

Oxychlorination Test Conditions

A locally built, lab scale fluidized bed reactor was employed. Approximately 300 g of catalyst was charged and controlled to temperature between 210° C. and 245° C. by means of resistance heating. The system was operated at atmospheric pressure. The feed gases $C_2H_4$, HCl and air or $N_2$ and $O_2$ were introduced to the reactor just below the catalyst bed. Feed rates were maintained using commercial mass flow controllers such that the fluidized bed contact time was approximately 25 seconds and the $HCl/C_2H_4/O_2$ molar feed ratio was approximately 1.96/1.0/1, respectively.

The reactants and products pass upwards through the fluidized bed to a disengagement zone which separates the catalyst particles from the product gases. The product gases are then transported through an enclosed system to gas sampling stations. When analyses were to be made it was essential that the reactor and all downstream sample lines were maintained above the dew point of the gases.

Catalyst samples were removed from the reactor during reaction conditions. A sample port located near the bottom of the reactor but above the point where the feed gases are introduced was opened and the catalyst sample taken into a clear glass vial and sealed.

The catalyst samples were extracted with toluene according to the following procedure:

Five grams of catalyst was placed in a 50 cc crimp vial. Toluene (25 ml) was added and the sample mechanically shaken for 7 hours and then allowed to stand for approximately 15 hours. The catalyst and solvent was filtered through #2 Whatman paper into a 6 dram amber vial. 2,4,8-Trichlorodibenzodioxin was added as an internal recovery standard. The sample was then evaporated to dryness. The residue was reconstituted in 2–3 ml isooctane, transferred to a 4 ml amber vial, and evaporated to dryness without heating. The residue was then extracted in 0.1 ml isooctane for analysis by GC.

Two methods of analysis by GC were employed. Qualitative screening was performed on an HP5890 series II GC equipped with an electron capture detector (ECD) and RTX-5 column. Quantitative analysis were performed on an HP5870 GC equipped with an HP 5790 mass selective detector and a 30 m XTI-5 capillary column (0.25 µm film). Sample size was 2 µl, and the column conditions were 70° C. for two minutes, 15° C./minute ramp to 300° C., and a soak time of 17.7 minutes. Detection limits were to 0.1 ng PCBs or PCDD/Fs per gram of catalyst removed from the reactor.

Quantitative data reported below are listed in units of ng/g on the catalyst. Values for PCBs with 8, 9, and 10 chlorine atoms are summed and reported as "PCBs". Under the heading "OCDD" and "OCDF" are the octachlorinated dibenzodioxins and octachlorinated dibenzofurans respectively. It is widely known in the art that the oxychlorination process favors the formation of the more highly chlorinated PCDF derivatives over the lower chlorinated and more environmentally suspect congeners.

Experiments were conducted on fresh catalyst, with catalyst previously used in the laboratory oxychlorination reactor, and with catalyst previously used in the laboratory oxychlorination reactor in the presence of added aromatic hydrocarbons and chlorinated aromatic hydrocarbons. Experiments were also performed to determine if chlorinated ethene derivatives would be transformed into aromatic compounds or their known precursors (derivatives of butadiene). In all cases, no evidence was found for the aromatization of $C_2$ hydrocarbons or for the production of PCBs or PCDD/Fs when the feed to the reactor contained only $C_2H_4$, HCl, $O_2$ and $N_2$.

EXAMPLE 1

Fresh Catalyst (Baseline)

A sample of a fresh oxychlorination catalyst of the type disclosed in U.S. Pat. No. 5,292,703 was extracted as outlined above. Qualitative and quantitative GC analysis indicated that fresh catalyst contained only minute levels of PCBs and PCDD/Fs. The levels of contamination found were in agreement with those reported in the literature. They are similar to the background levels found on a wide variety of commercial and non-commercial materials.

This analysis was repeated on 5 additional samples of fresh catalyst to establish a baseline. The results are summarized in Table 1 below. Units are listed in nanograms per gram of EDC produced (ng/g).

TABLE 1

| Catalyst | PCBs ng/g | OCDD (ng/g) | OCDF (ng/g) |
| --- | --- | --- | --- |
| 1-A | <0.1 | non-detected | –0.8 |
| 1-B | <5 | non-detected | <5 |
| 1-C | 3.0 | non-detected | 2.3 |
| 1-D | <1 | non-detected | <1 |
| 1-E | <1 | non-detected | <1 |
| 1-F | <1 | non-detected | <1 |

EXAMPLE 2

(Comparative)

A sample of fresh catalyst was used in the laboratory oxychlorination reactor operating at 225° C., with molar ratios of $HCl/C_2H_4/O_2$ controlled at 1.97/1.0/1.1, and with approximately 25 seconds of contact time. The HCl, ethylene, and air were quantitatively pre-treated for the removal of aromatic compounds. The catalyst was sampled and extracted as described above. Surprisingly, no evidence was found for elevated levels (compared to baseline experiments) of PCBs or PCDD/Fs on quantitative analysis of the catalyst particles. If unavoidable, de novo synthesis of polychlorinated aromatics was occurring, there would have been observed easily detectible increases in PCBs and/or PCDD/Fs on the catalyst particles. Therefore, with no aromatic compounds present in the air after treatment using a suitable means for eliminating aromatic compounds, the oxychlorination effluent contains reduced levels of PCBs and PCDD/Fs.

EXAMPLE 3

(Comparative)

The fresh catalyst was placed in the laboratory oxychlorination reactor at the above conditions. A mixture of aromatic hydrocarbons consisting mainly of xylenes and $C_3$-benzenes was introduced at a combined level of approximately 100 ppb based on the air feed rate. The reaction was conducted for approximately 24 hours to allow for a steady-state to be established, and the catalyst was sampled and analyzed as described above. GC-MSD results indicated elevated levels of PCBs and PCDD/Fs: PCBs=21.2 ng/g; OCDD=non-detected; OCDF=94.2 ng/g. In a similar experiment the following was observed: PCBs=23.9 ng/g; OCDD= non-detected; OCDF=14.6 ng/g. These observations illustrate that aromatic compounds present in the air stream do contribute to measurable amounts of polychlorinated aromatics above the baseline found in the oxychlorination effluent.

EXAMPLE 4

(Comparative)

Following the same procedure as in Example 3, benzene was introduced at a rate of approximately 7% of the air feed rate for 6 hours. The catalyst was sampled and analyzed as described above, and elevated levels of PCBs and PCDD/Fs were found: PCBs=5.3 ng/g; OCDD=not analyzed; OCDF= 1137 ng/g.

EXAMPLE 5

(Comparative)

Following the procedures for Example 4 above, toluene was introduced at a rate of approximately 2% based on the air feed. Analysis of the catalyst after about 6 hours of exposure gave the following results: PCBs=46.4 ng/g; OCDD=42.3 ng/g; OCDF=315.6 ng/g.

EXAMPLE 6

(Aromatization Test)

In an effort to determine if chlorocarbons can join to form butadiene and butadiene derivatives which are known to react with olefins to yield aromatic compounds, perchloroethylene was introduced to the laboratory oxychlorination reactor operating under conditions similar to those in Example 5. Qualitative analysis of the reaction product by GC-MSD indicated the presence of all the chlorinated derivatives of ethane and ethene. However, no evidence was found for $C_3$, $C_4$, or higher hydrocarbons or their derivatives. This indicates that there is no aromatization occurring under typical oxychlorination conditions. The catalyst type used in the above experiments is not unique in regard to the observed behavior and is merely illustrative of a typical oxychlorination catalyst in commercial use.

DISCUSSION

Example I illustrated that before usage in an oxychlorination reaction, fresh catalyst is seen to contain only trace quantities of PCBs and PCDD/Fs. Example 2 illustrated the surprising result that when all feed components used in the process are free of aromatic compounds and fresh catalyst is used, there is no de novo synthesis of PCBs and PCDD/Fs under the conditions which are suitable for industrial scale operation. There are advantages in preventing the formation of PCBs and PCDD/Fs from occurring in the oxychlorination process effluent since the heavy ends byproducts contained in the crude EDC and the waste water sludge accumulated from the process can now approach or achieve zero levels of PCBs and PCDD/Fs. There are considerable economic advantages of eliminating the steps of decontamination of the waste effluents. Environmental contamination ultimately is reduced.

In light of the above understanding, one can appreciate the application of the invention to other similar processes such as chlorination, hydrochlorination, and the reverse processes. The ability for prevention of formation of PCBs and PCDD/Fs can be realized for any industrial process involving chlorine, hydrogen chloride and aliphatic hydrocarbons, under conditions that prevent the conversion of aliphatic hydrocarbons to aromatic hydrocarbons. The present invention is not applicable to those processes where de novo synthesis of aromatic and polychlorinated aromatic compounds intrinsically occurs or where aromatic compounds are an integral part of the process.

We claim:

1. An improved process for manufacturing chlorinated hydrocarbon with reduced formation of chlorobenzenes, polychlorinated biphenyls (PCBs), polychlorinated dibenzodioxins (PCDDs) and polychlorinated dibenzofurans (PCDFs), said process starting with $C_1$ to $C_3$ hydrocarbon reactant selected from the group consisting of methane, ethane, ethylene, acetylene, propane, propylene, methylacetylene, and halogen substituted versions thereof, said process comprising: contacting said reactant with air or oxygen enriched air and hydrogen chloride, said contacting is conducted in the presence of a copper (II) oxychlorination catalyst in a heated reaction zone operating at from 150° C. to 600° C. wherein chlorinated hydrocarbon is recovered from the effluents of the reaction zone, the process is characterized by the fact that the air is pretreated with a means for removal of aromatic hydrocarbons.

2. The process of claim 1 wherein said means for removal of aromatic compounds from air is selected from the group consisting of distillation, adsorption, absorption, hydrogenation, and oxidation.

3. The process of claim 1 wherein said means for removal of aromatic compounds is selected from the group consisting of (a) passing said air through a vessel containing activated carbon, (b) treating said air with activated charcoal, (c) treating said air with silica, (d) treating said air with an aromatic compound adsorptive resin, (e) subjecting said air to a hydrogenation process, (f) extraction of said air with aliphatic liquid hydrocarbon, and (g) subjecting said air to an oxidation process.

4. The process of claim 1 wherein said hydrocarbon is selected from the group consisting of methane, ethane and propane and wherein said heated reaction zone is operated at from 300° C. to 600° C.

5. The process of claim 1 wherein said hydrocarbon is selected from the group consisting of ethylene, acetylene, propylene, and methylacetylene and wherein said heated reaction zone is operated at from 150° C. to 300° C.

6. The process of claim 1 wherein said hydrocarbon is ethylene.

* * * * *